United States Patent [19]

Horn et al.

[11] Patent Number: 4,562,196
[45] Date of Patent: Dec. 31, 1985

[54] 2,4-DIAMINOPYRIDINE AS A PHARMACOLOGIC AGENT

[75] Inventors: Alan S. Horn, Noordhorn; Sandor Agoston, Garrelsweer, both of Netherlands

[73] Assignee: Nelson Research & Development, Calif.

[21] Appl. No.: 597,732

[22] Filed: Apr. 6, 1984

[51] Int. Cl.$^4$ ...................... A61K 31/14; A61K 31/44
[52] U.S. Cl. ..................................... 514/332; 514/643
[58] Field of Search ................ 424/263, 324; 514/332, 514/643

[56] References Cited

PUBLICATIONS

Chem. Abst. 91-83512w (1979).
Chem. Abst. 96-173679p (1982).
Chem. Abst. 93-126282g (1980).

Primary Examiner—Stanley J. Friedman
Attorney, Agent, or Firm—Knobbe, Martens, Olson & Bear

[57] ABSTRACT

A method for inducing an anticurare response by administering 2,4-diaminopyridine to a mammal is disclosed, together with pharmaceutical compositions containing an effective amount of 2,4-diaminopyridine either alone or in combination with an anticholinesterase agent. 2,4-Diaminopyridine is an antagonist of muscle relaxants used in anesthesiology and can increase neuromuscular transmission in certain disease states.

13 Claims, No Drawings

2,4-DIAMINOPYRIDINE AS A PHARMACOLOGIC AGENT

BACKGROUND OF THE INVENTION

This invention relates generally to the compound 2,4-diaminopyridine (2,4-DAP), and more particularly to a method for using 2,4-DAP as an antagonist of certain muscle relaxants used during surgical operations and for the enhancement of neuromuscular transmission in certain disease states.

A number of muscle relaxants, typified by curare, find wide use in medicine and surgery. Curare, originally used as a poison for arrow tips by South American Indians, is routinely administered by anesthesiologists preparing patients for surgery. Curare acts as a muscle relaxant by decreasing neuromuscular transmission, thereby inducing paralysis at high dosages.

There is a corresponding need in anesthesiology for agents to reverse the effects of clinical muscle relaxants, preferably by facilitating or enhancing neuromuscular transmission. Moreover, such agents are potentially useful in the treatment of diseases which cause decreased neuromuscular transmission, such as botulism and myasthenia gravis, and as a reversal agent for certain antibiotics having a neuromuscular blocking action.

One compound that has been shown to be clinically useful in this regard is 4-aminopyridine (4-AP).

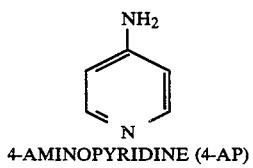

4-AMINOPYRIDINE (4-AP)

4-aminopyridine has been clinically used for several years, particularly in Bulgaria, as an antagonist of the action of some muscle relaxants used in anesthesiology. (Paskov et al., *Eksp. Khir Anaestesiol.* 18, 48–52 (1973)). In addition it has been shown that 4-AP potentiates anticholinesterase drugs (e.g. neostigmine and pyridostigmine) in their antagonistic action against neuromuscular blocking drugs used in surgery (Miller et al., *Anesthesiology* 50, 416–420 (1979)).

4-AP exerts a potassium channel blocking action in axonal membranes, prolonging nerve action potentials. This effect leads to an enhanced calcium ion influx and an increased release of neurotransmitters. Additionally, 4-AP has been used to reverse the neuromuscular block of several antibiotics, in the treatment of myasthenia gravis, the Eaton Lambert syndrome, botulism, Huntington's chorea, and even multiple sclerosis. It also antagonizes morphine-induced respiratory depression and ketamine-diazepam anesthesia.

Nevertheless, despite its continuing clinical use, 4-AP has a number of undesirable effects that limit its clinical usefulness. These effects stem from its central nervous system action. 4-AP causes enhanced autonomic and central transmission, leading, inter alia, to hypertension and convulsions at dosage levels only slightly exceeding the clinical dosage.

Some early experimental work has now been done with 3,4-diaminopyridine (3,4-DAP).

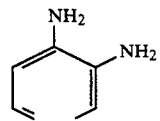

3,4-DIAMINOPYRIDINE (3,4-DAP)

This compound exhibits stronger peripheral action and less central action than 4-AP in vitro, most likely because it has more difficulty passing the blood-brain barrier. However, in vivo, the action of 4-AP and 3,4-DAP were almost the same (Durant, et al., *Eur. J. Pharmacol.* 84, 215–219 (1982)). Moreover, the $LD_{50}$ values for intraperotoneal 4-AP and 3,4-DAP in mice are 10 mg./kg. and 20 mg./kg., respectively (Vohra, et al. *J. Med. Chem* 8, 296–304 (1965)). The $LD_{50}$ dosage corresponds to a lethal dose in 50% of the animals treated. Thus, although not as toxic as 4-AP, 3,4-DAP suffers from the similar disadvantage of high toxicity at dosage levels near those that would be used in therapy. Like 4-AP, possible beneficial effects of 3,4-DAP at relatively high dosage levels cannot be explored because of its tendency to cause convulsions before such levels are reached.

Accordingly, there is a need for a muscle relaxant antagonist that has enhanced peripheral activity, less central action, and lower toxicity than 4-AP.

Therefore, it is an object of the invention to provide a method for antagonizing the actions of certain muscle relaxants resulting in enhanced peripheral activity and decreased central action. Another object of the invention is to provide a pharmaceutical composition containing an active muscle relaxant antagonist that is less toxic than 4-AP and 3,4-DAP.

SUMMARY OF THE INVENTION

It has been discovered that the compound 2,4-diaminopyridine (2,4-DAP) is a more effective pharmacological agent in many applications than either 4-AP or 3,4-DAP.

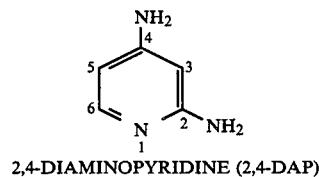

2,4-DIAMINOPYRIDINE (2,4-DAP)

Surprisingly, 2,4-DAP causes significantly less central stimulation than 4-AP and is far less toxic than either 4-AP or 3,4-DAP.

Accordingly, the present invention provides a method for selectively antagonizing the actions of certain muscle relaxants used in anesthesiology by administering to a mammal, such as a human, a clinically effective amount of 2,4-DAP either alone or in combination with an anticholinesterase agent such as neostigmine, edrophonium, or pyridostigmine.

In another aspect of this invention, there is provided a therapeutic composition for use in antagonizing the actions of muscle relaxants comprising an effective amount of 2,4-DAP or a pharmacologically acceptable salt thereof in combination with a pharmaceutically acceptable excipient.

Still another aspect of this invention relates to a method for treating certain neuromuscular disease states characterized by decreased neurotransmission, such as myasthenia gravis and botulism, by administering to a mammal an effective dosage of 2,4-DAP or a pharmaceutically acceptable salt thereof.

DETAILED DESCRIPTION OF PREFERRED EMBODIMENTS

As will be set out in further detail below, 2,4-DAP exhibits superior properties in standard animal tests over the clinical reference compound 4-AP. In addition, it has been discovered that the $LD_{50}$ value for 2,4-DAP is more than 200 mg./kg. (Volhra et al., supra). By comparison, 4-AP has an $LD_{50}$ of 10 mg./kg. and 3,4-DAP has an $LD_{50}$ of 20 mg./kg. (Id.) Thus, the two latter compounds are an order of magnitude more toxic than the compound of the present invention. Moreover, 2,4-DAP has not been shown to cause convulsions, presenting the possibility of therapeutic uses at much higher dosage levels than are possible with 4-AP or 3,4-DAP.

2,4-DAP is not a new compound, and its synthesis is known. It may readily prepared according to the method by Meyer and Tropsch, *Montasch. Chem.* 35, 189 (1914). In essence, the known compound 2,4-pyridinedicarboxylic acid is reacted with methanol in sulfuric acid to form the dimethylester. The dimethylester is reacted with hydrazine hydrate to give thee dihydrazide. Treatment of the dihydrazide with potassium nitrite in acid produces the 2,4-diazide of pyridine, which is refluxed in ethanol to produce the diethylurethane. Finally, hydrolysis with potassium hydroxide yields 2,4-diaminopyridine.

The synthesis of 2,4-diaminopyridine is set forth in greater detail in Example 1:

EXAMPLE I

Synthesis of 2,4-DAP 10 g. of 2,4-pyridinedicarboxylic acid (1) gave 8.5 g. of the dimethylester (2) following treatment with methanol in sulfuric acid. 8 g. of this diester (2) was converted to 6.5 g. of the dihydrazide (3) after reaction with hydrazine hydrate.

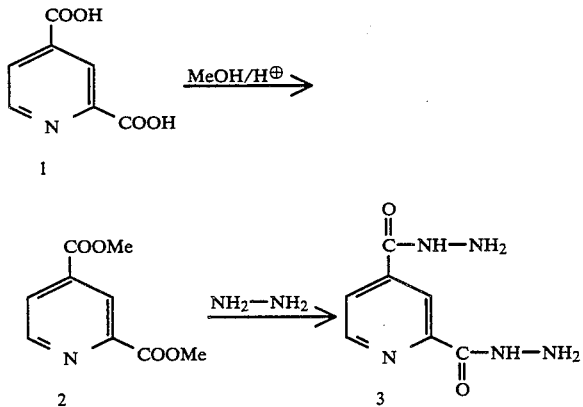

6 g. of the dihydrazide (3) on treatment with an acidic solution of potassium nitrite gave 4.7 g. of the diazide (4). 3.8 g. of (4) was refluxed in ethanol to yield 2.5 g. of the diethylurethane (5). Refluxing 2.5 g of (5) with a solution of ethanolic potassium hydroxide produced 1 g. of 2,4-diaminopyridine, (6).

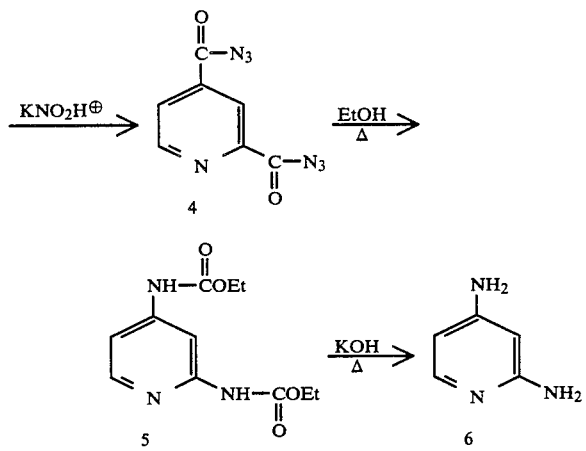

The resulting product had a melting point of 105°–107° C.

Pharmacological Compositions

The compound 2,4-DAP may be administered to a mammalian subject either alone or as an acid addition salt. Any of the conventional therapeutically acceptable acids may be used to make salts, such as hydrochloric acid, acetic acid, propionic acid, phosphoric acid, succinic acid, maleic acid, citric acid, or ascorbic acid.

2,4-DAP and the foregoing salts may also be formulated into pharmaceutical compositions with other ingredients, and may be provided in individual dosage units. Each unit may contain a pharmaceutically effective amount of active ingredient. The pharmaceutical composition may be in any form suitable for oral use, such as tablets, suspensions, dispersable powders, emulsions, capsules, or elixirs. Coloring, flavoring, sweetening, and preserving agents may also be provided.

Tablets containing the active ingredient or ingredients in admixture with non-toxic pharmaceutically acceptable excipients which are suitable for the manufacture of tablets are also within the scope of this invention. These excipients may be inert diluents, such as calcium carbonate, sodium carbonate, lactose, calcium phosphate; or binding agents, such as starch, gelatin, or acacia; or lubricating agents, such as magnesium stearate, stearic acid or talc. Moreover, oral compositions may be coated by known techniques to delay disintegration and absorption in the gastrointestinal tract, thereby providing sustained action.

Aqueous suspensions, containing conventional suspending agents, dispersing or wetting agents, preservatives, coloring agents, flavoring agents, and sweetening agents may be formulated in accordance with industry standards. Similarly, dispersable powders and granules for preparation of aqueous suspensions by the addition of water may be provided.

The compositions of this invention may be provided in individual dosage form to be administered orally or parenterally. Parenteral compositions may be provided containing the active composition and any of the well-known injectable carriers. The term parenteral as used herein includes subcutaneous injection, intravenous, intramuscular, or intrasternal injection, or infusion techniques.

Pharmaceutical Uses

The exact dosage of 2,4-DAP for any particular application may be readily determined by standard animal and clinical testing techniques. Dosage levels will generally be slightly lower than the corresponding clinical dosage levels for 4-AP (which are well-established) because of the greater activity of 2,4-DAP. The highest safe dosage of 4-AP for muscle-relaxant reversal is about 0.3 mg./kg. Uges, *4-Aminopyridine, Clinical Pharmaceutical, Pharmacological and Toxicological Aspects*, 178 (1982) (thesis). Long-term clinical dosages of 4-AP for treating disease states in humans are about 10 mg. 2-3 times daily. Id at 190. However, in appropriate situations, dosage levels an order of magnitude greater than those used for 4-AP may be used, because of 2,4-DAP's much lower toxicity. As a general rule, clinical dosages will be in the range of from 0.01 mg./kg. to 150 mg./kg. Pharmaceutical preparations in dosage form will preferrably contain from 1 mg. to 200 mg. of 2,4-DAP, and most preferrably from 5 mg. to 100 mg. of 2,4-DAP.

One of the preferred uses of the invention is in a pharmaceutical composition in admixture with an anticholinesterase agent. Preferred anticholinesterase agents are neostigmine and pyridostigmine. 2,4-DAP will complement and enhance the action of these drugs, and has a synergistic effect when used in combination therewith, particularly as an antagonist of muscle relaxants used in anesthesiology. Either oral or parenteral compositions of 2,4-DAP and the anticholinesterase drug may be made as set forth above.

From a comparison of animal and clinical experiments with 4-AP, particularly preferred compositions (based on the body weight of the patient) would contain about 0.5-1.0 mg./kg. 2,4-DAP and about 10-20 $\mu$g./kg. neostigimine or about 50-100 $\mu$g./kg. pyridostigmine. For a 50 kg. patient, a dosage-unit composition would include about 25-50 mg. 2,4-DAP and about 0.50 to 1.0 mg. neostigimine or about 2.5 to 5.0 mg. pyridostigmine.

Clinically, 2,4-DAP is administered to a mammal, such as a human, in a pharmacologically effective amount. In accordance with one embodiment of the invention, 2,4-diaminopyridine is administered to a mammal, such as a human, to antagonize the actions of certain muscle relaxants used in anesthesiology either alone or in combination with an anticholinesterase agent. In accordance with another method, 2,4-DAP is administered to a mammal, such as a human, that is suffering from a disease that decreases neurotransmission, such as myasthenia gravis or botulism, in an amount effective to increase neurotransmission. The pharmacological activity of 2,4-DAP will be illustrated through the following standard test procedures:

EXAMPLE 2

Rat Hemidiaphragm

This is a method of evaluating the antagonistic actions of muscle relaxants in vitro (Bowman, Kahn and Savage, *J. Pharm. Pharmacol.*, 29, 616 (1977). After the neuromuscular transmission is blocked with pancuronium bromide the antagonist is given and the resulting percentage antagonism of the pancuronium blockade is measured. From dose-response curves the $EC_{50}$'s (the concentration that produces a 50% antagonism) are calculated.

Left hemidiaphragms with their phrenic nerves were removed from male Wistar rats weighing 280-320 g. and were mounted in an organ bath, containing Krebs solution, maintained at 37° C. and gassed with oxygen containing 5% $CO_2$. The nerve was stimulated at a frequency of 0.1 $H_z$ via electrodes with rectangular pulses of 0.3 ms duration and of a strength greater than that required to reproduce maximal twitch. After equilibration for at least 30 min, pancuronium bromide (Pavulon ®) was added to the bath to produce a 90% block (concentration in the bath about $8 \times 10^{-6}M$). When a stable block of 5 min had been achieved, solutions of each drug were added to the bath, cumulatively.

Results $EC_{50}$ 4-Aminopyridine = $5.5 \times 10^{-5}$ mol/liter
$EC_{50}$ 3,4-Diaminopyridine = $1 \times 10^{-5}$ mol/liter
$EC_{50}$ 2,4-Diaminopyridine = $1.5 \times 10^{-5}$ mol/liter

Conclusion 2,4-Diaminopyridine has about the same potency as 3,4-diaminopyridine and is about 3.5 times more potent than 4-aminopyridine in this test model.

EXAMPLE 3

The Ileum Of The Guinea Pig

This preparation tests the pharmacological activity on smooth muscle (Moritoki, Takei, Makomoto and Ishida, *Arch. Int. Pharmacodyn. Ther.* 232, 28 (1978).

The concentration of the ileum was measured. This is compared to the maximal contraction caused by carbochol. From dose response curves the following $pD_2$ values were determined (the $pD_2$ value is the negative logarithm of the dose required to produce 50% of the maximum response).

Segments of guinea-pig ileum of 3 to 4 cm. length from 10 cm above the ileocaecal junction were used. The oral end of each segment was fixed to a hook and the distal end was connected to an isotonic transducer with a 1 g counterweight. The preparation was then immersed to an organ bath (25 ml) at 37° C. containing Krebs solution and bubbled with oxygen containing 5% $CO_2$. After an equilibration time of about 1 hour, $2 \times 10^{-7}M$ carbochol was added to the bath for maximal contraction. After wash out ($2 \times$) the drugs were added cumulatively to the bath.

Results $pD_2$ 4-Aminopyridine = 4.30
$pD_2$ 2,4-Diaminopyridine = 4.52.

Conclusion 2,4-Diaminopyridine is slightly more potent than 4-aminopyridine in this test model.

EXAMPLE 4

The Isolated Heart Of The Rat

This preparation evaluates the positive inotropic action of a drug (Koomen, van Gilst, Zimmerman and Noordwijk, *Arch. Int. Pharmacodyn. Ther.* 255, 212 (1982)).

Solutions of the aminopyridines were added to the perfusion solution of the rat heart. The left ventricular pressure (L.V.P.) was recorded in order to evalute the positive inotropic action. Frequency and E.C.G. were also monitored. Male Wistar rats (270-300 g) were anaesthetized with diethyl ether. After heparinization the hearts were quickly removed. Subsequently the heart was perfused according to the method of Langendorff. The perfusion fluid contained: NaCl 128 mM; KCl 4.7 mM; CaCl$_2$ 1.35 mM; MgCl$_2$ 1.05 mM; NaHPO$_4$ 0.42 mM; NaHCO$_3$ 20.2 mM; glucose 11.1 mM. The pH of the perfusion fluid after aeration with 95% O$_2$--5% CO$_2$ was 7.35±0.05 (37° C.). L.V.P. was measured by means of a catheter inserted in the left ventricule and connected to a pressure transducer. A biopolar E.C.G. was obtained by means of two silver electrodes: one attached to the metal inflow cannula and the other to the ventricular apex. Coronary flow (volume of perfusion fluid per time unit) was measured by a microprocessor, which controlled the perfusion pressure by adjusting the peristaltic perfusion pump.

Results

Over the concentration range $5 \times 10^{-6}$ mol/l to $10^{-4}$ mol/l, 2,4-diaminopyridine increased the L.V.P. up to 50%. In concentrations from $2 \times 10^{-5}$ to $1 \times 10^{-4}$ mol/l, 4-aminopyridine increased the L.V.P. up to 40%. No changes in frequency or E.C.G. were noted.

Conclusion 2,4-Diaminopyridine is significantly more effective than 4-aminopyridine in this test model.

EXAMPLE 5

The Rat Sciatic Nerve-Anterior Tibialis Preparation

This preparation is used to test the antagonistic action of aminopyridines against neuromuscular blocking agents in vivo. (Miller, Denissen, van der Pol, Agoston, Booy and Crul, *J. Pharm. Pharmacol.* 30, 699 (1978)).

Rats were administered a constant infusion of pancuronium bromide and when a constant block was achieved, one of the aminopyridines was administered. The ED$_{50}$'s (dose of drug producing a 50% antagonism) were determined.

Rats (280–320 g) were anaesthetized with pentobarbital. Both jugular veins were cannulated for administration of drugs. A caratoid artery was cannulated for measurement and recording of arterial blood pressure. The trachea was intubated and ventilation controlled by means of a Braun air pump. The tendon of the left tibialist was freed, sectioned and connected to a force displacement transducer. The sciatic nerve was stimulated by supramaximal 0.1 Hz stimuli of 0.2 msec duration through a bipolar electrode. Twitch tension was recorded on a polygraph. The temperature of the rat was maintained at 37° C. with heating lamps. Pancuronium bromide was administered intravenously by continuous infusion until 90-95% depression of twitch tension was obtained. This infusion speed was maintained during the whole experiment. When the block was steady for at least 15 min one of the drugs was given cumulatively with 10 min interval.

Results

ED$_{50}$ 4-Aminopyridine: 450 mg./kg.
ED$_{50}$ 3,4-Diaminopyridine: 250 mg./kg.
ED$_{50}$ 2,4-Diaminopyridine: 140 mg./kg.

Conclusion 2,4-Diaminopyridine is about 3 times more potent than 4-aminopyridine and about twice as potent as 3,4-diaminopyridine in this model.

EXAMPLE 6

Antagonism Of Ketamine-Xylazine Narcosis

This is a method of testing the central effects of the aminopyridines.

Rats were anaesthetized with xylazine (0.05 ml of a 2% soln, s.c.) and ketamine (0.1 ml of a soln, i.p.). After 10 min. the aminopyridines (1 mg./kg) were administered, i.v. The time required for "full recovery" (i.e. turning over and crawling) was measured. Groups of 10 rats were used for each treatment.

Recovery times

| | |
|---|---|
| saline control | 45 min. ± 10 min. |
| 4-Aminopyridine | 15 min. ± 7 min. |
| 3,4-Diaminopyridine | 35 min. ± 6 min. |
| 2,4-Aminopyridine | 44 min. ± 11 min. |

Conclusion

Rats treated with 2,4-diaminopyridine at 1 mg./kg. did not differ significantly from controls receiving saline, i.e., the central actions of 2,4-diaminopyridine following an i.p. injection are much weaker than those of 4-aminopyridine and somewhat weaker than those of 3,4-diaminopyridine.

General Conclusion 2,4-Diaminopyridine is more potent than 4-aminopyridine on several peripheral systems yet it is much weaker as an C.N.S. stimulant. Thus, the central side effects of 4-aminopyridine are expected to be largely absent in 2,4-diaminopyridine. 2,4-diaminopyridine also compares favorably with 3,4-diaminopyridine in peripheral activity and central stimulation. A further significant advantage with 2,4-diaminopyridine is the fact that it is much less toxic than either 4-aminopyridine or 3,4-diaminopyridine, i.e., in mice the LD$_{50}$'s are reported as >200 mg./kg. for 2,4-DAP, 10 mg./kg. for 4-AP, and 20 mg./kg. for 3,4-DAP (i.p.), (Vohra et al, *J. Med. Chem.*, 8, 296 (1965)).

We claim:

1. A method for enhancing neuromuscular transmission, comprising the step of administering to a subject having impaired neuromuscular transmission an amount of 2,4-diaminopyridine or a pharmaceutically acceptable salt thereof sufficient to enhance neuromuscular transmission.

2. The method of claim 1, wherein said impaired neuromuscular transmission has been pharmacologically induced.

3. The method of claim 2, wherein the 2,4-diaminopyridine or salt thereof is administered in combination with an anticholinesterase agent selected from the group consisting of pyridostigmine, neostigmine, and edrophonium.

4. The method of claim 3, wherein said anticholinesterase agent is neostigmine or pyridostigmine.

5. The method of claim 1, wherein said impaired neuromuscular transmission has been induced by a disease state.

6. The method of claim 1, wherein the amount administered is between about 0.01 mg. and 50 mg. per kg. of body weight.

7. The method of claim 6, wherein the amount administered is between about 0.1 mg. and 10 mg. per kg. of body weight.

8. A therapeutic composition, comprising, as an active ingredient, a clinically effective amount of 2,4-diaminopyridine or a pharmaceutically acceptable salt thereof, and a clinically effective amount of an anticholinesterase agent selected from the group consisting of pyridostigmine, neostigmine, and edrophonium, in an inert pharmaceutical carrier.

9. The composition of claim 8 in an individual dosage unit containing sufficient active ingredient to antagonize the action of a muscle relaxant.

10. The composition of claim 8, wherein said anticholinesterase agent is neostigmine or pyridostigmine.

11. The composition of claim 10, containing about 25 to 50 mg. 2,4-diaminopyridine and about 0.50 to 1.0 mg. neostigmine.

12. The composition of claim 10 containing about 25 to 50 mg. 2,4-diaminopyridine and about 2.5 to 5.0 mg. pyridostigmine.

13. The composition of claim 8, wherein said active ingredient is an amount sufficient to enhance neuromuscular transmission in a subject having impaired neuromuscular transmission.

* * * * *